(12) United States Patent  (10) Patent No.: US 7,768,645 B2
Roman  (45) Date of Patent: Aug. 3, 2010

(54) MINIATURE OPTICAL READHEAD AND COLORIMETER FOR ANALYSIS MEDIA

(75) Inventor: Juan F. Roman, St. Edmunds (GB)

(73) Assignee: Siemens Healthcare Diagnostics Inc., Tarrytown, NY (US)

(*) Notice: Subject to any disclaimer, the term of this patent is extended or adjusted under 35 U.S.C. 154(b) by 144 days.

(21) Appl. No.: 11/942,910

(22) Filed: Nov. 20, 2007

(65) Prior Publication Data

US 2009/0128816 A1    May 21, 2009

(51) Int. Cl.
 *G01J 3/51* (2006.01)
(52) U.S. Cl. .................. 356/406; 356/407; 356/419; 422/82.05
(58) Field of Classification Search ............ 356/405, 356/406, 407, 419
 See application file for complete search history.

(56) References Cited

U.S. PATENT DOCUMENTS

| | | | |
|---|---|---|---|
| 4,755,058 A | 7/1988 | Shaffer | |
| 5,279,294 A | 1/1994 | Anderson et al. | |
| 5,374,395 A | 12/1994 | Robinson et al. | |
| 5,408,535 A | 4/1995 | Howard, III et al. | |
| 5,724,148 A | 3/1998 | Howard, III et al. | |
| 6,055,060 A | 4/2000 | Bolduan et al. | |
| 6,184,040 B1 | 2/2001 | Polizzotto et al. | |
| 6,331,715 B1 | 12/2001 | Mauchen et al. | |
| 6,495,373 B1 | 12/2002 | Mauchen | |
| 7,339,673 B2 * | 3/2008 | Roman | 356/402 |
| 2007/0064220 A1 | 3/2007 | Stock et al. | |
| 2007/0183930 A1 * | 8/2007 | Roman | 422/82.05 |

FOREIGN PATENT DOCUMENTS

EP    0560410 B1    10/2002

OTHER PUBLICATIONS http://www.clearblue.info.
http://www.unipath.com/clearbluedigital.cfm.
Takao Someya and Takayasu Sakurai, "Opto&Laser Europe," Feb. 2005, pp. 22-23.

* cited by examiner

*Primary Examiner*—F. L Evans
(74) *Attorney, Agent, or Firm*—Richard L. Sampson; Noam R. Pollack (57) ABSTRACT

A miniature readhead is provided for photometric color detection using ambient light. The readhead is hand-held, including a superposed plate and tray. The tray receives sample media configured to react and to change color according to an amount of analyte in a sample. The plate is optically transmissive, so that ambient light is transmissible therethrough to the sample media indexed within the tray. An array of light detectors is disposed along the plate, including sets of detectors configured to detect light of at least three mutually distinct wavelengths reflected from the test areas. Light shields superposed with each of the light detectors selectively permit ambient light to pass to the tray, while substantially preventing ambient light from reaching the light detectors prior to reflecting from the test areas. The readhead may be incorporated into a photometric diagnostic instrument configured to analyze the reflections and derive a diagnosis value.

46 Claims, 5 Drawing Sheets

MINIATURE OPTICAL READHEAD AND COLORIMETER FOR ANALYSIS MEDIA

RELATED APPLICATIONS

This application is related to U.S. patent application Ser. No. 11/158,634 entitled Miniature Optical Read-head for Optical Diagnostic Device filed on Jun. 22, 2005, which is a Continuation-In-Part of co-pending P.C.T. Patent Application No. US05/07227, designating the United States, entitled Handheld Optical Diagnostic Device Having Image System Array, filed Mar. 3, 2005, which claims priority to U.S. Provisional Patent Application Ser. No. 60/550,811, entitled Handheld Optical Diagnostic Device Having Image System Array, filed on Mar. 5, 2004, all of which are fully incorporated by reference herein.

BACKGROUND

1. Technical Field

The present invention generally relates to the field of clinical chemistry. More particularly, the present invention relates to a compact readhead and optical diagnostic system that uses ambient light to analyze the color change associated with one or more test areas on sample media following contact thereof with a liquid specimen, such as urine, saliva, blood serum or whole blood.

2. Background Information

Throughout this application, various patents are referred to by an identifying citation. The disclosures of the patents referenced in this application are hereby incorporated by reference into the present disclosure.

Sample media such as reagent test strips are widely used in the field of clinical chemistry. A test strip usually has one or more test areas spaced along the length thereof, with each test area being capable of undergoing a color change in response to contact with a liquid specimen. The liquid specimen usually contains one or more constituents or properties of interest. The presence and concentrations of these constituents or properties are determinable by an analysis of the color changes undergone by the test strip. Usually, this analysis involves a color comparison between the test area or test pad and a color standard or scale. In this way, reagent test strips assist physicians in diagnosing the existence of diseases and other health problems.

Color comparisons made with the naked eye can lead to imprecise measurement. Today, strip reading instruments exist that employ reflectance photometry for reading test strip color changes. These instruments accurately determine the color change of a test strip within a particular wavelength range or bandwidth. Examples of such instruments include those sold under the CLINITEK® trademark by Siemens Medical Solutions Diagnostics (Tarrytown, N.Y.) and/or as disclosed in U.S. Pat. Nos. 5,408,535 and 5,877,863 (the '863 patent), both of which are fully incorporated by reference herein. These instruments are typically used to detect colors associated with a urine specimen on a MULTISTIX® (Siemens) reagent strip.

Another strip reading instrument utilizing reflectance photometry to read multiple test strips is disclosed in U.S. Pat. No. 5,055,261. An operator sequentially places test strips in a loading area. An arm orients the test strips on rails extending from the loading area to one or more reading stations employing readheads.

A common aspect of these instruments is that their relative size and complexity, particularly with respect to those utilizing automated test pad transport systems, render them relatively bulky and difficult to transport. Rather, these devices tend to be installed at a dedicated testing center or laboratory, where samples are aggregated and tested in bulk. Unfortunately, such aggregation of samples from multiple patients presents opportunities for error due to mislabeling of the samples and/or the test results. Moreover, in many instances, the time required for transporting the samples to and from the processing center, and for testing and recording the results, may be problematic.

A portable diagnostic device is described in U.S. Provisional Patent Application Ser. No. 60/550,811, entitled Handheld Optical Diagnostic Device Having Image System Array, filed Mar. 5, 2004, which is fully incorporated herein by reference. This device advantageously provides a portable means for analyzing the aforementioned reagent strips.

Other portable diagnostic devices include the Clearblue™ Digital Pregnancy Test device (Unipath Limited, UK) and the glucose test system disclosed in U.S. Pat. No. 6,055,060. These are generally single test devices, i.e., used to test for single analytes, such as the hCG hormone (pregnancy) or glucose. As such, these devices may be optimized for relatively narrow spectral (color) detection ranges, such as blue in the case of the Clearblue™ tester, and yellow/green for the glucose test system. Moreover, even with the relative simplicities inherent with such single analyte testing environments, these devices tend to utilize relatively complex readhead systems that may be labor intensive to manufacture.

In addition, most of the foregoing approaches rely on a relatively complex illumination scheme to provide carefully controlled levels and wavelengths of lighting in order to provide accurate color determination.

Another, relatively simple, portable imaging device has been disclosed by Takao Someya and Takayasu Sakurai, of the University of Tokyo, in "Opto & Laser Europe", February 2005, pages 22-23). This device is a mechanically flexible film scanner configured to capture black and white images from non-flat surfaces, such as of labels affixed to bottles. Illumination is provided by ambient lighting, which eliminates the complexity associated with the aforementioned carefully controlled on-board illumination. However, Someya, et al. teach that their device is capable of only black and white imaging, and thus is not capable of the accurate color determination needed in the field of medical diagnostic imaging. Moreover, Someya et al. disclose a relatively large sensor density, which would be expected to increase with the stated goal of increasing image resolution from the current 36 dots per inch (dpi) to a goal of 600 dpi. Such a large sensor density, however, leaves relatively small gaps therebetween, through which ambient light may pass to illuminate the label. This configuration therefore tends to create shadows on the label that would militate against using this approach to obtain the accurate color measurements that would be required for sophisticated medical diagnostic applications.

A need therefore exists for an inexpensive, portable, and mechanically rugged readhead and diagnostic testing device that enables a care provider to obtain quick and accurate test results for a range of analytes without the need for sending sample media to a remote testing center for processing. A need also exists for a readhead and portable diagnostic testing device of relatively low mechanical and electronic complexity, to provide for simplified manufacturability, and low power consumption to enable extended operation using a portable power supply.

SUMMARY

An aspect of the present invention includes a miniature readhead for a photometric diagnostic instrument for detecting color information from a target area using ambient light. The readhead includes a housing having a hand-held form factor, including a plate and a tray configured for being superposed with one another. The tray is configured for receiving reagent sample media having a plurality of test areas spaced thereon. Each of the test areas is configured to react with a sample when disposed in contact with the sample and to change color according to an amount of an analyte in the sample. The tray is sized and shaped for forming an indexed fit with the sample media. The plate is optically transmissive, so that ambient light is transmissible therethrough to the sample media indexed within the tray. An array of light detectors is disposed in spaced relation along the plate, the array including sets of light detectors configured to respectively detect light of at least three mutually distinct wavelengths. Each set is configured to receive diffuse, non-specular reflections of light from a respective one of the test areas when the sample media is indexed within the tray. Light shields are superposed with each of the light detectors to selectively permit ambient light to pass to the tray, while substantially preventing ambient light from reaching the light detectors prior to reflecting from the test areas. The readhead is thus operable without the use of any non-ambient light sources.

In a variation of the preceding aspect, the readhead is incorporated into a photometric diagnostic instrument including a processor operatively coupled to the light detectors. The processor is configured to analyze the reflections received by the light detectors, to derive a diagnosis value from the analysis, and to generate an output corresponding thereto.

In another aspect of the invention, a method is provided for reading reagent sample media having a plurality of test areas disposed in spaced relation thereon, each of the test areas configured to react with a sample when disposed in contact with the sample and to change color according to an amount of an analyte in the sample. The method includes receiving the sample media into a sample tray of a readhead of a photometric diagnostic device, the readhead having a hand-held form factor, including a plate and a tray configured for being superposed with one another, the tray configured for receiving reagent sample media in an indexed fit therewith, the plate being optically transmissive, so that ambient light is transmissible therethrough to the sample media indexed within the tray. The method further includes exposing the readhead to ambient light so that the sample media is illuminated by ambient light transmitted through the plate. Diffuse, non-specular reflectances of the test areas and then capturing by respective sets of light detectors within an array of ambient light detectors, the sets configured to respectively detect light of at least three mutually distinct ambient light wavelengths. Ambient light is nominally prevented from reaching the array of light detectors prior to reflecting from the test areas. The color of the non-specular reflectances is determined, which is then used to deriving the amount of an analyte in the sample. An output signal corresponding to the amount of analyte is then generated.

In still another aspect of the invention, a miniature readhead for a photometric diagnostic instrument for detecting color information from a target area using ambient light, is provided. The readhead includes housing means having a hand-held form factor, the housing means including plate means and tray means configured for being superposed with one another, the tray means configured for receiving reagent sample media therein. The sample media has a plurality of test areas each configured to react with a sample when disposed in contact with the sample and to change color according to an amount of an analyte in the sample. The tray is sized and shaped for forming an indexed fit with the sample media. The plate means is optically transmissive, so that ambient light is transmissible therethrough to the sample media indexed within the tray. A light detection means is disposed along the plate means, and includes sets of light detectors configured to respectively detect light of at least three mutually distinct wavelengths. Each set is configured to receive diffuse, non-specular reflections of light from a respective one of the test areas when the sample media is indexed within the tray. Light shield means are superposed with each of the light detectors to selectively permit ambient light to pass to the tray, while substantially preventing ambient light from reaching the light detectors prior to reflecting from the test areas. The readhead is thus operable without the use of any non-ambient light sources.

BRIEF DESCRIPTION OF THE DRAWINGS

The above and other features and advantages of this invention will be more readily apparent from a reading of the following detailed description of various aspects of the invention taken in conjunction with the accompanying drawings, in which.

DETAILED DESCRIPTION

In the following detailed description, reference is made to the accompanying drawings that form a part hereof, and in which is shown by way of illustration, specific embodiments in which the invention may be practiced. These embodiments are described in sufficient detail to enable those skilled in the art to practice the invention, and it is to be understood that other embodiments may be utilized. It is also to be understood that structural, procedural and system changes may be made without departing from the spirit and scope of the present invention. The following detailed description is, therefore, not to be taken in a limiting sense, and the scope of the present invention is defined by the appended claims and their equivalents. For clarity of exposition, like features shown in the accompanying drawings are indicated with like reference numerals and similar features as shown in alternate embodiments in the drawings are indicated with similar reference numerals.

Figure 1:
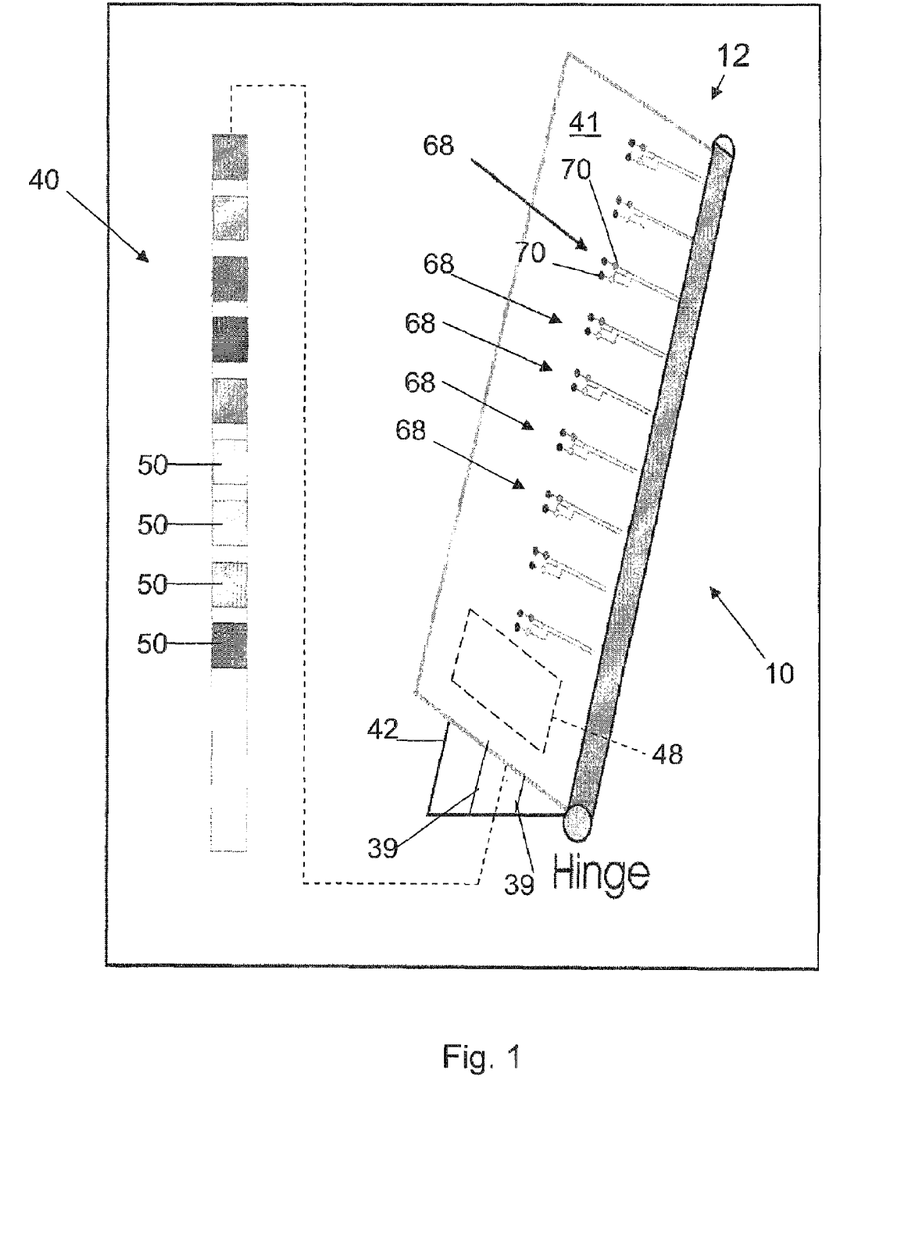
FIG. 1 is a partially exploded schematic view of an embodiment of the readhead of the present invention in an open position, along with a sample media strip usable therewith.
Figure 2:
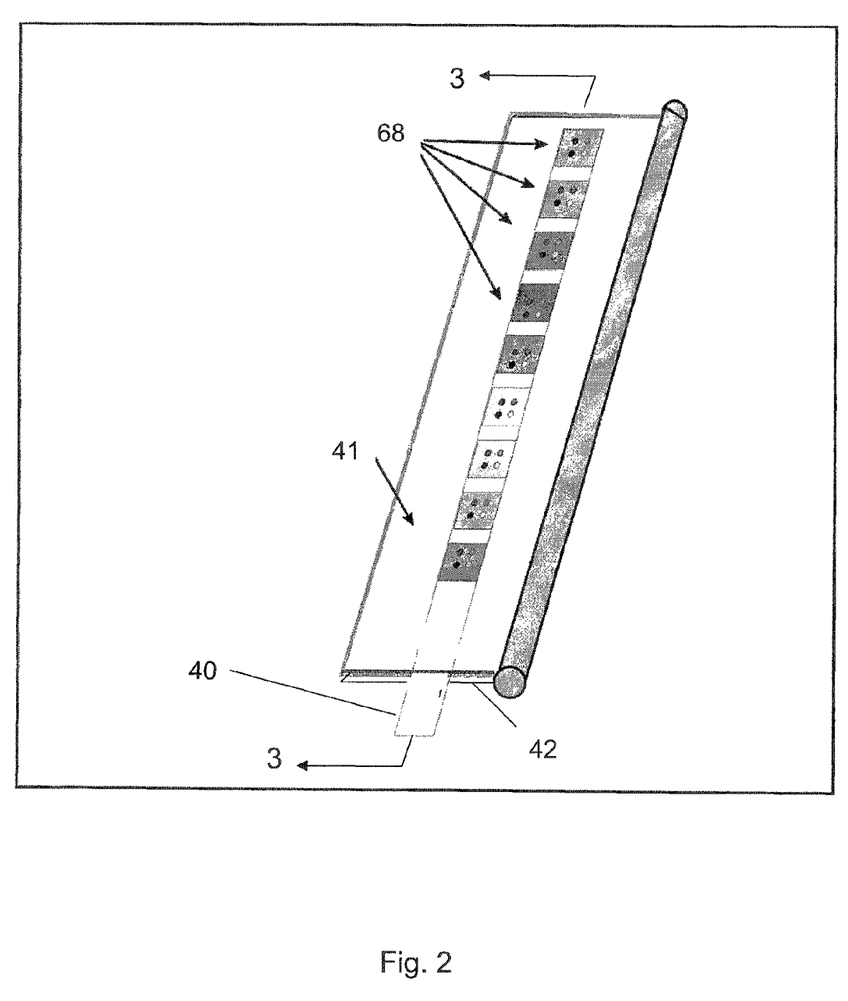
FIG. 2 is a schematic view of the embodiment of FIG. 1, in a closed position with a sample media strip in operative engagement therewith.
Figure 3:
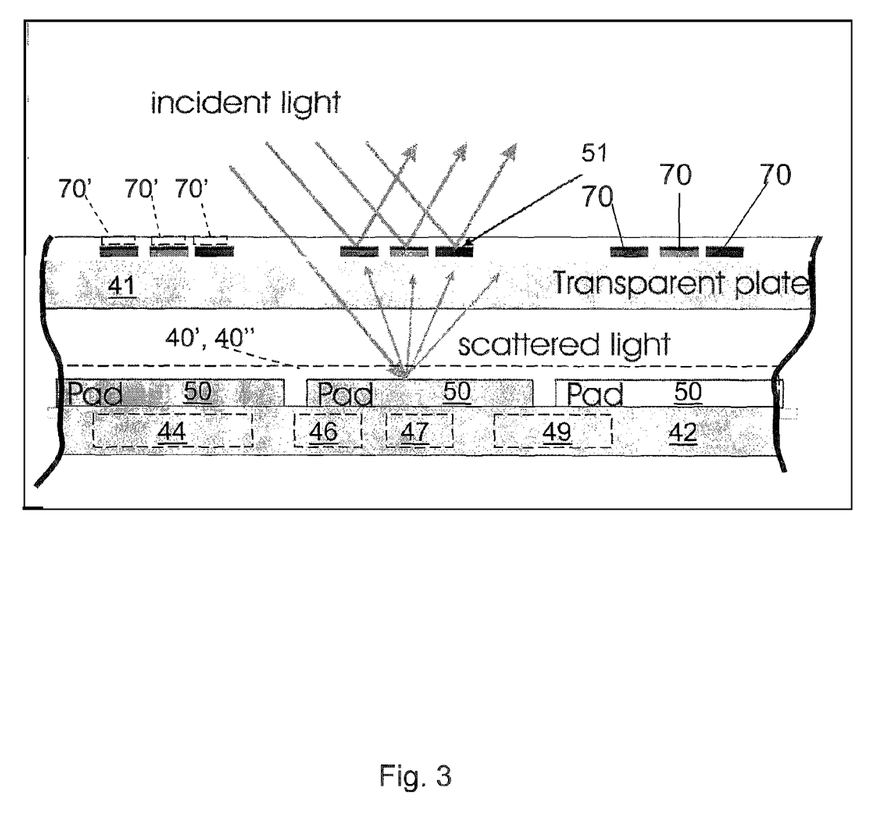
FIG. 3 is a cross-sectional, on an enlarged, not-to-scale view of an embodiment similar to that of FIGS. 1 and 2, having sets of three detectors, taken along 3-3 of FIG. 2, showing a field of view of the detectors, and having optional aspects shown in phantom.

An overview of an embodiment of the invention is provided with reference to FIGS. 1-3. This embodiment includes a miniature readhead 10 for a photometric diagnostic instrument capable of detecting color information from a target area of a reagent sample media such as the above-referenced MULTISTIX® test strip, using ambient light. In the embodiment shown, readhead 10 includes a planar housing 12 in the form of a cover plate 41 hingedly coupled to a tray 42. The plate 41 is optically transmissive, i.e., transparent or translucent, to facilitate illumination of the test areas 50 by ambient light passing therethrough.

The tray 42 may also be optically transmissive, or may be tinted with a predetermined color that may be used to calibrate the instrument upon start up as discussed hereinbelow. The tray 42 may be sized and shaped for forming an indexed fit with the sample media 40. Tray 42 may also be provided with a length corresponding to the length of test strip 40, so that proper insertion of media 40 will be achieved once all of the test areas 50 are superposed with plate 41. Alternatively, an optical or mechanical sensor may be used to ensure that the strip has been fully inserted.

An array of light detectors (color detection means) 70 is arranged in sets 68 of three or more detectors 70 sensitive to mutually distinct colors of light. The sets 68 are pitched to match that of the test areas (e.g., pads) 50 of the sample media (e.g., test strip) 40. These sets 68 are disposed to respectively detect diffuse reflections from each of the test areas 50 when the sample media is indexed within tray 42, such as shown in FIG. 2.

Notably, as best shown in FIG. 2, the small number of detectors 70 (e.g., as few as three detectors for red, green and blue detection) in each set 68, provides a relatively low detector density per unit area of test area 50. Such low density provides a relatively large open area through which ambient light may enter and pass through plate 41 to illuminate the test areas 50 without the excessive shadow effects that would be generated by the relatively high sensor density associated with high resolution, black and white imaging schemes.

The hinged arrangement of cover 41 relative to tray 42, and/or the elimination of any on-board illumination, enables the cover to be disposed in close proximity to pads 50, such as in substantial physical contact therewith. This close proximity enables each set 68 of detectors to receive light from its respective test area 50, nominally without receiving stray reflectances from other test areas 50, to effectively eliminate cross-talk. Moreover, adverse effects such as interference typically associated with specular reflections from sample media 40 are substantially prevented by the use of diffuse, ambient lighting instead of on-board light sources. The plate 41 may also be optionally tinted to further diffuse or filter the incoming ambient light. Light shields 51 (FIG. 3) superposed with each light detector 70 selectively permit ambient light to pass therebetween to the tray, while substantially preventing ambient light from reaching detectors 70 prior to reflecting from the test areas as shown in FIG. 3.

Readhead 10 may be coupled in any convenient manner (e.g., port 46) to a conventional instrument such as the aforementioned CLINITEK® instrument to capture and analyze the color information from the test areas 50. Alternatively, in particular embodiments, readhead 10 may be provided with an integral processor 44 and power supply 49 (FIG. 3) and display 48 (FIG. 1), to form a complete, unitary diagnostic instrument. In these alternate embodiments, processor 44 is thus coupled to the detectors to analyze the captured reflectances (colors), derive a diagnosis value from the analysis, and to generate an output corresponding thereto. The output may be fed to the integral display 48, and/or wirelessly or via port 46 (FIG. 3), to a remote display.

As is familiar to those skilled in the art, sample media 40 may include typical urine analysis strips, having paper pads disposed in spaced relation thereon, which are soaked in chemical reagents that react with a specimen sample to change color according to the medical condition of the patient, i.e., according to levels of various analytes in the sample. As used herein, the term 'analyte' refers to a constituent, or to a property (e.g., pH) of the sample. Examples of such media 40 include the aforementioned MULTISTIX® test strips. Alternatively, sample media 40 may include a conventional immuno-assay cassette, e.g., the CLINITEST® hCG cassette (Siemens), (such as shown schematically in phantom as 40' in FIG. 3), having an area soaked in chemical reagents that react to the sample to reveal a colored line or pattern of lines according to the medical condition of the patient.

Other suitable sample media may include conventional microfluidic devices (such as shown schematically as 40" in FIG. 3) which typically include a substrate having a series of narrow channels, e.g. on the order of microns in width, through which a fluid such as blood or urine may travel. The channels conduct the fluid to various test areas on the device. These devices enable various tests to be performed using only a small amount of fluid, e.g., using a small drop of liquid. Exemplary microfluidic devices are described in U.S. patent application Ser. No. 10/082,415 filed on Feb. 26, 2002 and entitled Method and Apparatus For Precise Transfer And Manipulation of Fluids by Centrifugal and or Capillary Forces.

The embodiments discussed herein thus provide a particularly small, planar form factor, suitable for handheld, battery powered operation. This small, generally planar form factor is provided in part, by the use of ambient lighting and diffuse reflectance color detection to eliminate the need for complex imaging technology. Ambient lighting further reduces the form factor of readhead 10 by eliminating the need for on-board lighting arrays, which permits the light detectors 70 to be placed in closer proximity to pads 50, e.g., with the plate nominally superimposed with the pads. Moreover, there is no need for a form factor large enough to provide adequate physical separation between the sample media and on-board light sources. Such close proximity also reduces the possibility of optical cross-talk, which substantially eliminates the need for complex structures to prevent light from being reflected to adjacent sensor sets 68, to enable further reduction in the form factor of readhead 10. Thus, elimination of on-board lighting, the close proximity of the detectors to the pads, and the manner in which color detection is effected as discussed hereinbelow, tends to simplify processing to advantageously reduce processing overhead, while providing high reliability.

This construction also eliminates the relatively large power requirements associated with on-board lighting systems, for extended battery life. Still further, these embodiments provide for embedding the various components, including sensors 70 and other circuit elements, etc., within the plate 41 and/or tray 42, to provide a rugged, compact device that may be easily carried in care provider's pocket, and which may be easily cleaned by placement under running water, etc., and may operate for extended periods before replacing or recharging batteries. These embodiments thus provide an inexpensive, portable, and mechanically rugged readhead and diagnostic testing device that enable a care provider to obtain quick and accurate test results for a range of analytes without the need for sending sample media to a remote testing center for processing.

For convenience and clarity, various embodiments of the present invention are described as using sample media 40 in the form of MULTISTIX® test strips, with the understanding that substantially any form of sample media may be used without departing from the spirit and scope of the present invention. Embodiments of the present invention may be particularly beneficial when used with alternate media such as immuno-assay cassettes due to their often faint or otherwise difficult to read results.

Software associated with the various embodiments of the present invention can be written in any suitable language, such as C++; Visual Basic; Java; VBScript; Jscript; BCMAscript; DHTM1; XML and CGI. Any suitable database technology may be employed, including but not limited to versions of Microsoft Access and IMB AS 400.

Aspects of the various embodiments of the present invention will now be described in detail. Turning to FIGS. 1-3, in particular embodiments, readhead 10 includes a housing 12 including plate 41 and tray 42 conveniently formed as molded (e.g., injection molded) components hingedly coupled to one another. (The hinge may be placed longitudinally as shown, i.e., substantially parallel to an inserted strip 40 as shown. Alternatively, the hinge may be placed at either end of housing 12.) Tray 42 may include an elongated recess, such as defined by elongated ridges or abutments 39 spaced to provide a sliding fit with sample media (e.g., test strip) 40 as shown, inserted therebetween.

In the embodiment shown, sample media 40 includes a reagent strip having a predetermined number of test areas (e.g., reagent pads) 50 thereon. Each reagent pad 50 includes a relatively absorbent material impregnated with a respective reagent, each reagent and reagent pad 50 being associated with a particular test to be performed. When urinalysis tests are performed, they may include, for example, a test for leukocytes in the urine, a test of the pH of the urine, a test for blood in the urine, etc. When each reagent pad 50 comes into contact with a urine sample, the pad changes color, depending on the reagent used and the characteristics of the sample. As discussed above, reagent strip 40 may be a MULTISTIX® reagent strip commercially available from Siemens Corporation. The sample media may alternatively include an immuno-assay cassette 40' or a microfluidic device 40" as shown in phantom.

Referring now to FIG. 3 in particular, an ambient light source, such as sunlight or conventional interior office lighting, provides relatively diffuse incident light that passes through the optically transmissive (e.g., transparent or translucent) plate 41 to illuminate the pads 50. This incident light is then further diffused upon reflection from each pad 50 back towards the light sensitive faces of its respective set 68 of light detectors 70.

The light detectors 70 may be solid state devices such as conventional photodiodes. In the embodiment shown, each set 68 includes at least three detectors 70, configured (e.g., with filters) for detection of the colors Red, Green, Blue, respectively. Optionally, more than three detectors with narrower band filters may be used, such as the sets 68 of four detectors shown in FIGS. 1 and 2, may be desired in some embodiments, to facilitate more precise color measurements as discussed hereinbelow. As discussed hereinabove, the light detectors 70 are spaced along the length of plate 41, so that each set 68 is nominally centered on a respective reagent pad 50 as shown. These detectors 70 may be surface mounted on plate 41, either on the external surface, or on the internal surface where they may be placed in physical contact with the test pads 50. Alternatively, detectors 70 may be embedded within the plate as shown. This embedded configuration tends to protect the sensors and associated circuitry from mechanical damage, while also enabling the device to be conveniently cleaned, such as by immersing in water, etc., as discussed in greater detail hereinbelow. The plate 41 is placed on top of the strip, very close to the strip or in superimposed contact with it, with the sensors 70 oriented towards the strip.

Although photodiodes may conveniently be used, detectors 70 may alternately include any of a variety of other types of light detection devices known to those skilled in the art. As one example, each set 68 of detectors 70 may include a TCS230 detector commercially available from TAOS, Inc., e.g., with its packaging modified to provide enough room between sensors for ambient light to reach pads 50. The TCS230 device includes filters of three colors (RGB) superposed with an array of individual light sensors. The TCS230 generates a digital output, via an integral analog-to-digital converter, to obviate any need for subsequent signal conversion. This device is also relatively compact, having an active area of 1.15×1.15 mm.

As mentioned above, the ambient light scattered from the pads 50 will have a different color depending on the reaction that took place on the chemical reagents. This particular pad color may be calculated by capturing the output of the sensors 70 of each set 68 using processor 44, and with the processor, calculating the ratio of these captured outputs for each detector set 68. (Note that for clarity, electrical connections between the detectors 70 and processor 44 have been omitted from the figures. It should be understood, however, that such connections may be embedded within, or printed on the various surfaces the plate 41 and/or tray 42. Moreover, although processor is shown as embedded within tray 42, it may be disposed substantially anywhere within the housing, including plate 41, e.g., in a position that does not prevent ambient light from reaching any of the pads 50.) In this way color can be measured without the need for on-board, artificial light sources, such as LED's, simply using ambient light such as from the sun or from artificial lighting. These embodiments thus effectively mimic the manner in which the human eye measures color, by relying on ambient light to illuminate the object and then calculating the ratio between various detectors of mutually distinct wavelengths.

Optionally, the readhead may include a series of secondary detectors 70' disposed on plate 41 (or embedded therein as shown), such as at either end of the strip 40, or superposed with detectors 70 as shown. These secondary detectors 70' may be equipped with transmission color filters similar to those placed on the detectors 70. However, the light sensitive surfaces of these secondary detectors 70' are faced away from pads 50 and towards the source of ambient light. These secondary detectors are operated in a manner similar to that of detectors 70, but measure the spectral content (color) of the ambient light prior to reflection from pads 50. This measurement of the incident light may then be used by processor 44 to adjust (see step 86, Table I below) the pad color determined using the output of detectors 70, to nominally remove any uncertainty that may be caused by non-white ambient light, e.g. reddish-yellow when using tungsten lamps, bluish when using fluorescent tubes, or sunlight at dawn.

As mentioned above, plate 41 may include printed circuits (FIG. 1) that connect sensors 70, 70' to other components of the instrument, including processor 44 and power supply (e.g., battery) 49. The plate 41 and tray 42 may be fabricated from glass or any of various polymeric materials with the electrical circuit elements embedded on the plastic or printed thereon. The plate 41 and/or tray 42 may be flexible or rigid, substantially transparent, translucent, and/or tinted with color. Tints on the plate 41 may be used for aesthetic purposes, to help control the wavelengths of ambient light incident on pads 50, and/or to help reduce specular reflection by helping to diffuse incoming ambient light. The colors of the pads 50 as determined by various embodiments of the present invention may then be adjusted to account for the value of any such tint in a manner that will be understood to those skilled in the art in light of the instant disclosure. Such adjustment or calibration may be effected in a manner similar to that used in the CLINITEK STATUS® instrument commercially available from Siemens. As mentioned above, tray 42 may be tinted with a predetermined color, so that the tray itself may serve as an integral calibration standard.

The result of the color calculations is analyzed by means of reagent decodes to produce as a final result a quantitative analysis of the reaction on the reagent, in a manner similar to that effected in the CLINITEK STATUS® instrument, and as discussed in greater detail hereinbelow with respect to Table I and FIGS. 4 & 5.

In accordance with the foregoing, embodiments of readhead 10 may be provided with a relatively small form factor, similar in length to that of a MULTISTIX® test strip 40 as shown in FIG. 1, i.e., equal to or less than about 100 mm, with a width equal to or less than about 10 mm, and a thickness equal to or less than about 10 mm. In particular embodiments, the readhead may be provided with a length equal to or less than about 85 mm, a width equal to or less than about 5 mm, and a thickness equal to or less than about 5 mm. In still further embodiments, the readhead may be nominally as narrow as a MULTISTIX® test strip 40, e.g., approximately 5 mm, though it may be wider to permit greater overlap of the plate 41 over the strip 40 as shown. As discussed hereinabove, the use of ambient lighting, to obviate any need for on-board illumination, enables the array of detectors 70, 70' to be placed relatively close to the pads 50, to enable the height of plate 41 to be as little as about 2 mm.

Accordingly, readhead 10 (e.g., without the some of the optional components discussed hereinabove) may be easily incorporated into a variety of photometric diagnostic instruments, such as a CLINITEK® instrument. In such a configuration, readhead 10 may be electrically coupled to the instrument, which would supply power and operate the readhead 12 in a conventional manner, as will be described hereinbelow. When so incorporated, nominally any ambient lighting may be used to illuminate readhead 10, including natural light or artificial light generated by sources associated with the instrument.

Alternatively, readhead 10 may be provided with additional components, as shown in phantom in FIGS. 1 & 3, including for example, one or more of processor 44, memory 47, an output port 46, integral display 48, and a power supply (e.g., battery) 49. These additional components 44, 46, 48, 49 may be integrated into housing 12, to form a unitary handheld photometric diagnostic instrument, for an overall form factor that may be conveniently carried in a pocket by a health care provider.

Referring now to Table I, exemplary operation of an embodiment of the present invention is described. Initially, strip 40 is dipped in urine and placed 80 on tray 42. The plate 41 is then lowered 81 over the strip 40, so that it completely covers it and remains at a small distance from, or in physical contact with the strip as shown in FIG. 2. The sensors 70 of a particular set 68 (FIG. 1) are then actuated 82 to detect how much light passes through each filter, with the sensor output being captured by processor 44. Optionally, set(s) 68' of sensors 70', if provided, may be similarly actuated at 83 to capture sensor output associated with the color of the incident ambient light. The sensor output captured at 82 (and optionally, 83) may be optionally stored 84 to optional memory 47 (FIG. 3). This captured sensor output may then be used (e.g., by processor 44) to calculate 85 the ratio between the sensor output of set 68 (FIG. 1) to determine the color of pad 50. Optionally, this color determination may be adjusted 86 to compensate for the color of the ambient light determined at 83, and/or for any tint 41 applied to plate 41. The processor may also analyze 87 the color information, such as by comparing the captured color information to a database of known color-coded diagnostic values. Steps 80-87 may be repeated 88 for additional test areas (pads) 50. When the strip has been on the tray 42 long enough for the reagents on all pads 50 to have had time to react, and the colors thereof have been measured, the processor (e.g., 44) may optionally prompt 90 the user to remove the strip and wash the instrument. In the event the sensors 70, 70' and the various other components and circuitry are embedded within housing 10, washing may be accomplished conveniently, e.g., by simply placing the device under running water.

TABLE I

| | |
|---|---|
| 80 | Strip placed on tray |
| 81 | Lower plate |
| 82 | Sensor set 68 actuated to detect and capture levels of reflected ambient light at various wavelengths |
| 83 | Optionally actuate sensors 70' to detect and capture levels of ambient light |
| 84 | Optionally store information captured at 82 and/or 83 to memory |
| 85 | Calculate ratio of the captured sensor output to determine color, and optionally, color of ambient light |
| 86 | Optionally adjust determination of pad color based on color of ambient light and/or tint of plate 41 |
| 87 | Analyze color information |
| 88 | Repeat steps 80-87 for additional test areas |
| 90 | Optionally prompt user to remove strip 40 |

Additional operational aspects of embodiments of the invention are substantially similar to those of conventional photometric diagnostic instruments such as the above-referenced CLINITEK® instrument, and/or as described in the above referenced U.S. Provisional Patent Application Ser. No. 60/550,811. Such operational aspects are briefly described with respect to FIGS. 4 & 5.

Figure 4:
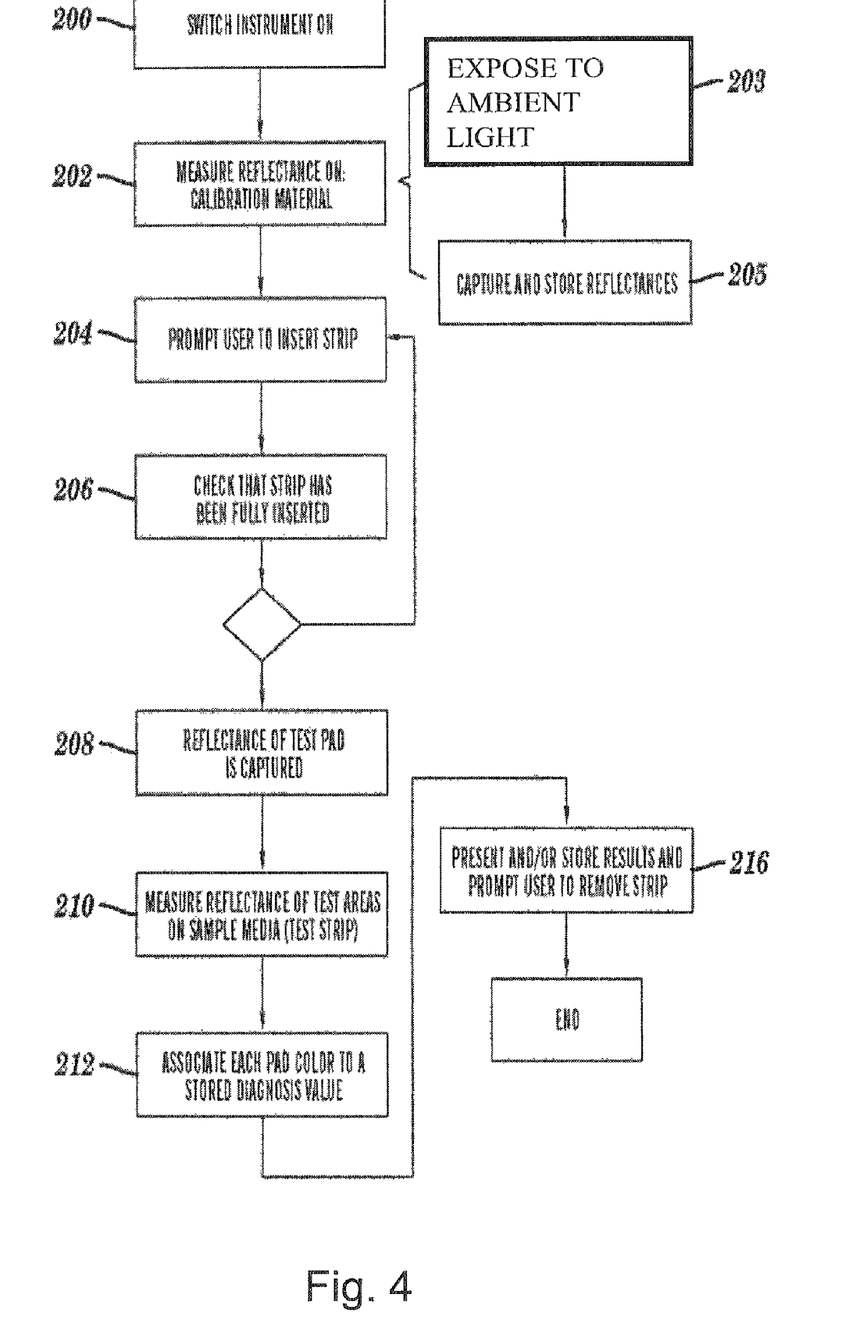
FIG. 4 is a flow chart of operational aspects of embodiments of the present invention.

Turning to FIG. 4, the instrument, including readhead 10, is initially powered up at 200, after which reflectance of calibration material is measured at 202. Calibration 202 may be effected automatically, e.g., each time the instrument is powered up 200, or may be initiated by the user who inserts a calibration material, for example, in response to an audible or visual prompt. Calibration may be effected by insertion of a discrete calibration material, or optionally by simply using the (tinted) tray 42 as the calibration material as mentioned hereinabove.

Calibration 202 includes exposing 203 the calibration material to ambient light, and capturing and storing 205 the responses of sensor set 68 to reflectance from the calibration material (e.g., per step 85 of Table I above). These calibration reflectances may then be used to effect sample measurement 210 as discussed in detail below with respect to FIG. 5.

Once calibration is complete, the instrument may prompt 204 the user to insert sample media 40, 40', 40" into tray 42. Upon insertion, the system checks 206 for an appropriate signal, e.g., from one or more of detectors 70, (or alternatively from nominally any other electromechanical switch or actuator) indicating that sample 40 has been fully inserted. If this signal has not been received, then the system loops back to step 204 to re-prompt the user to fully insert the sample. If the signal was received, then reflectances from a test pad are captured 208 and measured 210, and compared to calibration values generated during calibration 202, such as also described in greater detail with respect to FIG. 5.

At 212, these reflectance values are used to calculate the colors of the pads (e.g., per 85 of Table I), and are compared to known diagnosis values stored in memory (e.g., 47) as at 87 of Table I. At 216, results (i.e., diagnosis values) generated at 212 are then outputted to a display (e.g., 48) and/or stored to memory, and the user prompted to remove the strip.

Figure 5:
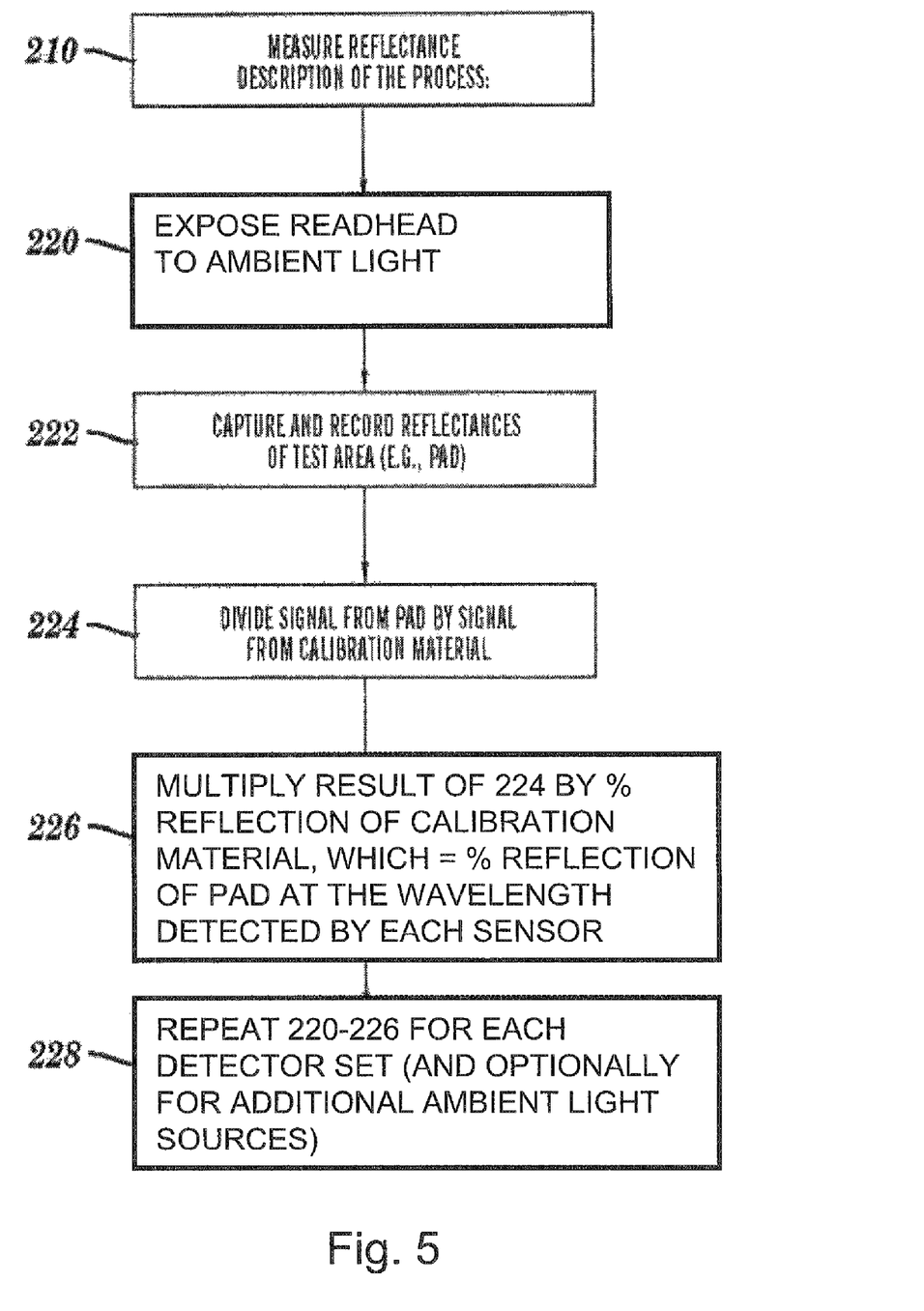
FIG. 5 is a flow chart of measurement steps effected during the operation of FIG. 4.

Turning now to FIG. 5, measurement 210 for a representative embodiment of the present invention is discussed in greater detail. As shown, such measurement includes exposing 220 the readhead 10 to an ambient light source. This ambient light source is preferably the same as that used during steps 203 and 205 of the calibration discussed above. The steps 80-84 of Table I are effected relative to sample media 40, 40', 40" etc., with the reflectance values captured at 82 for each pad 50 being saved to memory at 222. At 224, a numerical value of these captured reflectance is divided by a numerical equivalent of the corresponding reflectance values of the calibration material acquired at step 205 above. At 226, the results of step 224 are multiplied by the known percent reflections of the calibration material to generate the percent reflection of the particular pad or portion of sample 40, etc., at the known wavelength of each sensor within set 68 (FIG. 1). The ratio of these percent reflectances to one another are calculated per 85 of Table I, to determine the color of the pad(s) that may then be correlated to known diagnosis values as at 87 and 212 above.

As shown at 228, steps 220-226 may be repeated for each portion of interest of the sample media (e.g., each test pad), and optionally, for various ambient light sources.

In the preceding specification, the invention has been described with reference to specific exemplary embodiments thereof. It will be evident that various modifications and changes may be made thereunto without departing from the broader spirit and scope of the invention as set forth in the claims that follow. The specification and drawings are accordingly to be regarded in an illustrative rather than restrictive sense.

Having thus described the invention, What is claimed is:

1. A miniature readhead for a photometric diagnostic instrument for detecting color information from a target area using ambient light, the readhead comprising:

a housing having a hand-held form factor, including a plate and a tray configured for being superposed with one another, said tray configured for receiving reagent sample media therein, the sample media having a plurality of test areas disposed in spaced relation thereon, each of the test areas configured to react with a sample when disposed in contact with the sample and to change color according to an amount of an analyte in the sample;

the tray sized and shaped for forming an indexed fit with the sample media;

said plate being optically transmissive, wherein ambient light is transmissible therethrough to the sample media indexed within the tray;

an array of light detectors disposed in spaced relation along said plate;

said array including sets of light detectors configured to respectively detect light of at least three mutually distinct wavelengths;

each set configured to receive diffuse, non-specular reflections of light from a respective one of the test areas when the sample media is indexed within said tray;

a plurality of light shields superposed with each of said light detectors to selectively permit ambient light to pass to the tray, while substantially preventing ambient light from reaching the light detectors prior to reflecting from the test areas; and said readhead being operable free of any non-ambient light sources.

2. The readhead of claim 1, wherein said plate and said tray are substantially planar and hingedly coupled to one another.

3. The readhead of claim 1, wherein the ambient light is selected from the group consisting of sunlight or artificial light.

4. The readhead of claim 1, having a length equal to or less than about 100 mm, a width equal to or less than about 10 mm, and a thickness equal to or less than about 10 mm.

5. The readhead of claim 4, having a length equal to or less than about 85 mm, a width equal to or less than about 5 mm, and a thickness equal to or less than about 5 mm.

6. The readhead of claim 1, wherein said light detectors are embedded within said plate.

7. The readhead of claim 1, wherein said plate is configured for being superimposed with the sample media.

8. The readhead of claim 1, wherein said plate is optically transparent to visible light.

9. The readhead of claim 1, wherein said plate is optically translucent to visible light.

10. The readhead of claim 1, wherein said sets of light detectors comprise light detectors respectively coupled with filters configured to transmit light of the at least three mutually distinct wavelengths.

11. The readhead of claim 10, wherein the at least three mutually distinct wavelengths comprise red, green, and blue wavelengths.

12. The readhead of claim 1, wherein said housing is adapted for incorporation within a photometric diagnostic instrument.

13. The readhead of claim 1, wherein said light detectors are configured to receive diffuse, non-specular reflections of the light associated with a range of distinct analytes.

14. The readhead of claim 1, wherein said array of light detectors comprises an array of photodiodes.

15. The readhead of claim 1, wherein said array of light detectors comprises an array of CMOS devices.

16. The readhead of claim 1, comprising a memory device operatively engaged with said light detectors.

17. A photometric diagnostic instrument for detecting color information from a target area using ambient light, the instrument comprising:

a miniature readhead including:

a housing having a hand-held form factor, including a plate and a tray configured for being superposed with one another, said tray configured for receiving reagent sample media therein, the sample media having a plurality of test areas disposed in spaced relation thereon, each of the test areas configured to react with a sample when disposed in contact with the sample and to change color according to an amount of an analyte in the sample;

the tray sized and shaped for forming an indexed fit with the sample media;

said plate being optically transmissive, wherein ambient light is transmissible therethrough to the sample media indexed within the tray;

an array of light detectors disposed in spaced relation along said plate;

said array including sets of light detectors configured to respectively detect light of at least three mutually distinct wavelengths;

each set configured to receive diffuse, non-specular reflections of light from a respective one of the test areas when the sample media is indexed within said tray;

a plurality of light shields superposed with each of said light detectors to selectively permit ambient light to pass to the tray, while substantially preventing ambient light from reaching the light detectors prior to reflecting from the test areas; and said readhead being operable free of any non-ambient light sources;

a processor operatively coupled to said light detectors;

said processor configured to analyze the reflections received by said light detectors; and said processor configured to derive a diagnosis value from said analysis, and to generate an output corresponding thereto.

18. The instrument of claim 17, wherein said processor is disposed integrally with said housing.

19. The instrument of claim 18, comprising an integral display.

20. The instrument of claim 19, comprising an integral power supply, wherein said instrument is a hand-held, unitary device.

21. The instrument of claim 17, wherein said processor is configured to capture signals from the light detectors, and to calculate a ratio of the signals within each of said sets, to determine color reflectances from each of test areas.

22. The instrument of claim 21, wherein said plate is provided with a tint, and said processor is configured to adjust the color reflectances to compensate for said tint.

23. The instrument of claim 21, wherein said determination of color reflectances is automated.

24. The instrument of claim 21, wherein said array comprises an other set of light detectors configured to directly receive the ambient light, and said processor is configured to capture signals generated by said other set to determine a color of the ambient light.

25. The instrument of claim 24, wherein said other set comprises light detectors configured to respectively detect light of at least three mutually distinct wavelengths, said processor is configured to capture signals from the light detectors and calculate a ratio of the signals to determine the color of the ambient light.

26. The instrument of claim 24, wherein said processor is configured to adjust the color reflectances to compensate for the color of the ambient light.

27. The instrument of claim 17, wherein said light detectors are configured to receive diffuse, non-specular reflections of the light, said reflections being associated with a range of distinct analytes.

28. The instrument of claim 17, comprising a memory device coupled to said light detectors.

29. The instrument of claim 28, wherein said memory device is configured for storing diagnostic data.

30. The instrument of claim 29, wherein said memory device is configured for storing calibration data.

31. The instrument of claim 28, wherein said memory device is configured to store the reflections received by said light detectors.

32. The instrument of claim 17, wherein said diagnosis value comprises a quantitative measurement of said analyte.

33. The instrument of claim 17, wherein said diagnosis value comprises a diagnosis of a condition.

34. The instrument of claim 17, wherein said sample media includes a test strip, and said test areas include test pads.

35. The instrument of claim 17, wherein said sample media comprises an immuno-assay cassette.

36. The instrument of claim 17, wherein said sample media comprises a microfluidic device.

37. The instrument of claim 17, being free of an integral light source.

38. The readhead of claim 1, wherein said array includes sets of light detectors configured to respectively detect light of at least four mutually distinct wavelengths.

39. A method for reading reagent sample media, the sample media having a plurality of test areas disposed in spaced relation thereon, each of the test areas configured to react with a sample when disposed in contact with the sample and to change color according to an amount of an analyte in the sample, the method comprising:

(a) receiving the sample media into a sample tray of a readhead of a photometric diagnostic device, the readhead having a hand-held form factor, including a plate and a tray configured for being superposed with one another, said tray configured for receiving reagent sample media in an indexed fit therewith, said plate being optically transmissive, wherein ambient light is transmissible therethrough to the sample media indexed within the tray;

(b) exposing the readhead to ambient light wherein the sample media is illuminated by ambient light transmitted through the plate;

(c) capturing diffuse, non-specular reflectances of the test areas with respective sets of light detectors within an array of ambient light detectors disposed in spaced relation along said plate, said sets configured to respectively detect light of at least three mutually distinct ambient light wavelengths;

(d) preventing ambient light from reaching the array of light detectors prior to reflecting from the test areas during said capturing (c);

(e) determining the color of the non-specular reflectances;

(f) deriving the amount of an analyte in the sample from said determining (e); and (g) generating an output signal corresponding to the amount.

40. The method of claim 39, wherein the sample media is selected from the group consisting of test strips, immuno-assay cassettes, and microfluidic devices.

41. The method of claim 39, further comprising the step of calibrating the array of light detectors.

42. The method of claim 41, wherein said calibrating comprises effecting steps (b)-(e) for a calibration material of known color reflectance.

43. The method of claim 42, wherein said determining (e) comprises:

dividing the reflectances in each of the wavelengths of a test pad by the reflectances of the calibration material at the respective wavelengths;

multiplying the results of said dividing by known percent reflectances of the calibration material to generate a calibrated percent reflectance of the test pad at each of the wavelengths; and calculating a ratio of the calibrated percent reflectances to one another, to determine the color of the test areas.

44. The method of claim 43, wherein said deriving (f) comprises comparing the calibrated percent reflectance with known values of amounts of said analyte at various predetermined percent reflectances, to determine the amount of said analyte at said calibrated percent reflectance.

45. A miniature readhead for a photometric diagnostic instrument for detecting color information from a target area using ambient light, the readhead comprising:

said housing means having a hand-held form factor;

said housing means including plate means and tray means configured for being superposed with one another, said tray means configured for receiving reagent sample media therein, the sample media having a plurality of test areas disposed in spaced relation thereon, each of the test areas configured to react with a sample when disposed in contact with the sample and to change color according to an amount of an analyte in the sample;

the tray sized and shaped for forming an indexed fit with the sample media;

said plate means being optically transmissive, wherein ambient light is transmissible therethrough to the sample media indexed within the tray;

light detection means disposed in spaced relation along said plate means;

said light detection means including sets of light detectors configured to respectively detect light of at least three mutually distinct wavelengths;

each set configured to receive diffuse, non-specular reflections of light from a respective one of the test areas when the sample media is indexed within said tray;

light shield means superposed with each of said light detectors to selectively permit ambient light to pass to the tray, while substantially preventing ambient light from reaching the light detectors prior to reflecting from the test areas; and said readhead being operable free of any non-ambient light sources.

46. A miniature photometric diagnostic instrument comprising:

the miniature readhead of claim 45;

processing means operatively coupled to said light detection means;

said processing means configured to analyze the reflections received by said light detection means;

said processing means configured to derive a diagnosis value from said analysis, and to generate an output corresponding thereto; and said instrument being operable free of any non-ambient sample illumination.

* * * * *